United States Patent [19]

Fechtig et al.

[11] Patent Number: 4,873,322
[45] Date of Patent: Oct. 10, 1989

[54] SACCHARIDE DERIVATIVES AND PROCESSES FOR THEIR MANUFACTURE

[75] Inventors: Bruno Fechtig, Reinach; Gerhard Baschang, Bettingen, both of Switzerland

[73] Assignee: Ciba-Geigy Corporation, Ardsley, N.Y.

[21] Appl. No.: 3,986

[22] Filed: Jan. 16, 1987

[30] Foreign Application Priority Data

Jan. 24, 1986 [CH] Switzerland ............... 276/86

[51] Int. Cl.$^4$ ........................................... A61K 37/00
[52] U.S. Cl. .................... 536/4.1; 536/17.1; 536/17.5; 536/17.9
[58] Field of Search ............. 536/4.1, 17.1, 17.5, 536/17.9; 514/24, 25

[56] References Cited

U.S. PATENT DOCUMENTS

| | | | |
|---|---|---|---|
| 2,436,699 | 2/1948 | Rose | 260/403 |
| 2,447,715 | 8/1948 | Rose | 260/326 |
| 3,663,235 | 5/1972 | Menz | 99/123 |
| 3,862,121 | 1/1975 | Jaques et al. | 514/825 |
| 4,082,735 | 4/1978 | Jones et al. | 260/112.5 R |
| 4,082,736 | 4/1978 | Jones et al. | 260/112.5 R |
| 4,119,714 | 10/1978 | Kny et al. | 424/199 |
| 4,235,792 | 11/1980 | Hsia et al. | 260/403 |
| 4,254,115 | 3/1981 | Dawidson et al. | 424/211 |
| 4,323,560 | 4/1982 | Baschang et al. | 424/177 |
| 4,372,949 | 2/1983 | Kodama et al. | 424/199 |
| 4,386,026 | 5/1983 | Ponpipom et al. | 536/53 |
| 4,406,890 | 9/1983 | Tarcsay et al. | 424/177 |
| 4,414,204 | 11/1983 | Tarcsay et al. | 424/177 |
| 4,423,038 | 12/1983 | Baschang et al. | 424/177 |
| 4,426,330 | 1/1984 | Sears | 268/483 |
| 4,426,525 | 1/1984 | Hozumi et al. | 546/22 |
| 4,493,832 | 1/1985 | Teraji | 424/199 |
| 4,534,899 | 8/1985 | Sears | 260/403 |
| 4,548,923 | 10/1985 | Hartmann et al. | 514/8 |
| 4,607,011 | 8/1986 | Kaplan et al. | 435/131 |
| 4,624,919 | 11/1986 | Kokusho et al. | 536/4.1 |
| 4,666,893 | 5/1987 | Tsuchiya | 514/78 |
| 4,739,043 | 4/1988 | Defaye et al. | 536/18.4 |

FOREIGN PATENT DOCUMENTS

| | | |
|---|---|---|
| 138558 | of 1983 | European Pat. Off. |
| 72111 | 2/1983 | European Pat. Off. |
| 72286 | 2/1983 | European Pat. Off. |
| 99578 | 2/1984 | European Pat. Off. |
| 102319 | 3/1984 | European Pat. Off. |
| 118316 | 9/1984 | European Pat. Off. |
| 641811 | 5/1984 | Switzerland |
| 1530138 | 10/1978 | United Kingdom |
| 2051069 | 1/1981 | United Kingdom |

OTHER PUBLICATIONS

Derwent Abstract of European 175,290 Published (1980).
Derwent Abstract of German 3415102 (4/84).
Derwent Abstract of Japanese 52-087221 (1977).
Chem. Abstr. 69:958906 (1968).
Chem. Abstr. 71:123473e (1969).
Chem. Abstr. 66:95388g (1967).
Jour. Immunol. Methods 65:295-306 (1983).

*Primary Examiner*—Ronald W. Griffin
*Attorney, Agent, or Firm*—Irving M. Fishman; JoAnn Villamizar

[57] ABSTRACT

Mono- and di-saccharidyl derivatives that are linked via a bridge member to a cephalin derivative, of the formula I, and processes for their manufacture are described.

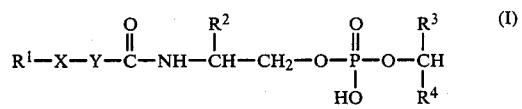

In the formula, $R^1$ represents (a) aldohexosyl, (b) D-aldohexosyl that is glycosidically linked in the 4- or the 6-position to D-aldohexosyl, (c) aldopentosyl, (d) 6-deoxyaldohexosyl or (e) 2-acetylamino-2-deoxy-D-aldohexosyl, it being possible for free hydroxy groups present in the radicals mentioned under (a) to (e) above to be peracetylated, X represents oxygen or sulphur, Y represents alkylene having up to 10 carbon atoms in which from 1 to 3 non-terminal methylene groups may be replaced by oxygen, by carbonylimino or by carbonyloxy, $R^2$ represents hydrogen, carboxy, lower alkoxycarbonyl, benzyloxycarbonyl or carbamoyl, $R^3$ represents hydrogen and $R^4$ represents a 1,2-dihydroxyethyl, 2-hydroxy-ethyl or hydroxymethyl group in which at least one hydroxy group is esterified by an unsubstituted aliphatic $C_{10-24}$-carboxylic acid and in which the other hydroxy group, if present, is free or esterified by an aliphatic $C_{2-24}$-carboxylic acid, or $R^3$ and $R^4$ each represents a hydroxymethyl group esterified by an unsubstituted aliphatic $C_{10-24}$-carboxylic acid. These compounds can be used as medicaments, for example for the prophylaxis and therapy of virus infections.

27 Claims, No Drawings

SACCHARIDE DERIVATIVES AND PROCESSES FOR THEIR MANUFACTURE

The invention relates to mono- and di-saccharidyl derivatives that are linked via a bridge member to a cephalin derivative, to processes for their manufacture, to pharmaceutical preparations containing these derivatives and to the use thereof as medicaments.

The invention relates especially to saccharide derivatives of the formula I

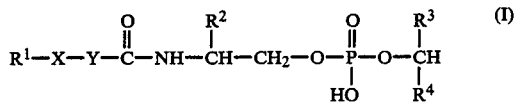

in which $R^1$ represents (a) aldohexosyl, (b) D-aldohexosyl that is glycosidically linked in the 4- or the 6-position to D-aldohexosyl, (c) aldopentosyl, (d) 6-deoxyaldohexosyl or (e) 2-acetylamino-2-deoxy-D-aldohexosyl, it being possible for free hydroxy groups present in the radicals mentioned under (a) to (e) above to be peracetylated, X represents oxygen or sulphur, Y represents alkylene having up to 10 carbon atoms in which from 1 to 3 non-terminal methylene groups may be replaced by oxygen, by carbonylimino or by carbonyloxy, $R^2$ represents hydrogen, carboxy, lower alkoxycarbonyl, benzyloxycarbonyl or carbamoyl, $R^3$ represents hydrogen and $R^4$ represents a 1,2-dihydroxyethyl, 2-hydroxy-ethyl or hydroxymethyl group in which at least one hydroxy group is esterified by an unsubstituted aliphatic $C_{10-24}$-carboxylic acid and in which the other hydroxy group, if present, is free or esterified by an aliphatic $C_{2-24}$-carboxylic acid, or $R^3$ and $R^4$ each represents a hydroxymethyl group esterified by an unsubstituted aliphatic $C_{10-24}$-carboxylic acid, and to salts of these compounds.

Aldohexosyl $R^1$ is L- or preferably D-aldohexosyl, especially D-glucosyl, D-mannosyl or D-galactosyl, preferably β-D-glucopyranosyl, α-D-mannopyranosyl or β-D-galactopyranosyl. D-aldohexosyl that is glycosidically linked in the 4- or the 6-position to D-aldohexosyl is preferably D-cellobiosyl, D-lactosyl or D-maltosyl, especially β-D-cellobiopyranosyl, β-D-lactopyranosyl or β-D-maltopyranosyl.

Aldopentosyl $R^1$ is D-aldopentosyl, for example D-arabinosyl, or L-aldopentosyl, for example L-arabinosyl.

6-deoxy-aldohexosyl $R^1$ is D-fucosyl or preferably L-fucosyl, especially β-L-fucopyranosyl.

2-acetylamino-2-deoxy-D-aldohexosyl $R^1$ is, for example, 2-acetylamino-2-deoxy-D-glucosyl, preferably 2-acetylamino-2-deoxy-β-D-glucopyranosyl.

As examples of the above-mentioned radicals $R^1$ in which free hydroxy groups are peracetylated there may be mentioned especially 2,3,4,6-tetra-O-acetyl-D-glucosyl and 2,3,4,6-tetra-O-acetyl-D-mannosyl, for example 2,3,4,6-tetra-O-acetyl-β-D-glucopyranosyl and 2,3,4,6-tetra-O-acetyl-α-D-mannopyranosyl.

In the above-mentioned hexosyl and pentosyl radicals $R^1$, the free valency extends from the carbon atom in the 1-position.

Alkylene Y is branched, it being possible for the two free valencies to extend from any carbon atoms, or preferably is unbranched (straight-chained). Alkylene Y has preferably up to 6, especially from 1 to 5, for example from 3 to 5, carbon atoms and is, for example, methylene or trimethylene. Alkylene Y in which from 1 to 3 non-terminal methylene groups, for example one methylene group, has or have been replaced by oxygen, carbonylimino or carbonyloxy is, for example, 2,5-dioxa-hexamethylene, $CH_2$—$CH_2$—$CH_2$—$C(=O)$—$NH$—$CH_2$— or —$CH_2$—$CH_2$—$CH_2$—$C(=O)$—$O$—$CH_2$—. In this case, carbonylimino preferably represents the group —CO—NH— but may also represent the group —NH—CO—, and carbonyloxy preferably represents the group —CO—O— but may also represent the group —O—CO—.

Lower alkoxycarbonyl $R^2$ is, for example, methoxycarbonyl.

The configuration at the C(—$R^2$) atom is (D) or preferably (L).

An unsubstituted aliphatic $C_{10-24}$-carboxylic acid is branched or preferably unbranched, has an uneven or preferably an even number of carbon atoms and is especially an alkanoic or alkenoic acid having from 10 to 24 carbon atoms, for example capric acid (n-decanoic acid), lauric acid, myristic acid, palmitic acid, stearic acid, arachidic acid (n-eicosanoic acid) or oleic acid. Alkanoic acids having from 10 to 20, especially from 12 to 18, carbon atoms and alkenoic acids having 18 carbon atoms and from 1 to 3 isolated double bonds, especially naturally occurring fatty acids, are preferred. An aliphatic $C_{2-24}$-carboxylic acid is especially a lower alkanoic acid, for example acetic acid, or one of the above-mentioned $C_{10-24}$-carboxylic acids.

To indicate the configuration at the central carbon atom of the substituted glycerol moiety of compounds of the formula I in which $R^3$ represents hydrogen and $R^4$ represents a 1,2-dihydroxy-ethyl group in which at least one hydroxy group is esterified, in accordance with the IUPAC rules, the stereospecific numbering of the carbon atoms of the glycerol moiety, characterised by the prefix "sn", is used. The uppermost carbon atom in the Fischer projection of the vertical carbon chain, in which the hydroxy group at the 2-carbon atom is on the left, is given the number 1. In the mentioned compounds according to the invention, the phosphoric acid group is bonded to the 3-carbon atom according to stereospecific numbering.

The proton bonded via oxygen to the phosphorus atom is acidic and can readily be removed with bases and replaced by another cation. At a pH value of 7, therefore, the compounds of the formula I are completely or predominantly in salt form. The invention relates also to these salts and to the acid-salt mixtures. The compounds of the formula I in which $R^2$ represents carboxy may form mono- or di-salts. The invention relates especially to pharmaceutically acceptable, non-toxic salts of compound of the formula I. These are especially metal or ammonium salts, such as alkali metal and alkaline earth metal salts, for example sodium, potassium, magnesium or calcium salts, or salts with ammonia or suitable organic amines, there being suitable for the salt formation especially aliphatic, cycloaliphatic, cycloaliphatic-aliphatic or araliphatic primary, secondary or tertiary mono-, di- or polyamines, and also heterocyclic bases, such as lower alkylamines, for example triethylamine, hydroxy-lower alkylamines, for example 2-hydroxy-ethylamine, bis-(2-hydroxyethyl)-amine, 2-hydroxy-ethyl-diethylamine or tri-(2-hydroxyethyl)-amine, basic aliphatic esters of carboxylic acids, for example 4-amino-benzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline.

For isolation or purification it is also possible to use pharmaceutically unacceptable salts. Only the pharmaceutically acceptable non-toxic salts are used therapeutically, however, and these are therefore preferred.

The general definitions used hereinbefore and hereinafter preferably have the following meanings:

The term "lower" denotes radicals having up to and including 7, especially up to and including 4, carbon atoms and, in the case of multiple radicals occurring as one word, refers only to the radical that immediately follows, that is to say, for example, in the case of lower alkoxycarbonyl, only to alkoxy. Including the carbonyl group, lower alkoxycarbonyl can therefore have up to 8 carbon atoms.

Halogen is especially chlorine or bromine, also fluorine or iodine.

The compounds of the formula I have valuable pharmacological properties. According to the invention, it has surprisingly been found that the above-mentioned compounds of the formula I and their pharmaceutically acceptable salts are outstandingly suitable both for the prophylaxis and for the therapy of virus infections as is apparent, for example, from tests on animals as given by way of illustration in the Examples. In these animal tests, animals such as mice or guinea pigs are infected with the most varied types of virus at a dosage that is lethal for all or the great majority of the untreated (control) animals, for example $LD_{80-90}$, and the course of the infection in the untreated control animals is observed in comparison with animals that have been treated with one of the above-mentioned compounds or a salt thereof before, simultaneously with or after infection.

In these tests, it is found that a prophylactic effect is achieved even when the compounds of the formula I are administered several days up to some weeks, for example four weeks, before infection, and that a therapeutic effect is still achieved when the compounds are administered several days, for example one week, after infection.

The compounds of the formula I are effective in the above-mentioned test in mice even in a dosage range of from 0.001 mg/kg to 1 mg/kg.

Also noteworthy is the broad spectrum of viruses against which the above-mentioned compounds are effective.

The compounds of the formula I can be used especially for the prophylaxis and therapy of diseases caused by the viruses specified below [see J. L. Melnick, Prog. med. Virol. 26, 214–232 (1980) and 28, 208–221 (1982) for nomenclature]: DNA viruses with cubic symmetry and naked nucleocapsid, DNA viruses with encapsulated virion and RNA viruses with cubic symmetry and those with helical symmetry of the capsid.

The compounds of the formula I are preferably used in the case of DNA viruses with encapsulated virion and cubic symmetry of the capsid, in the case of RNA viruses with cubic symmetry of the capsid and naked virion and in the case of RNA viruses with helical symmetry of the capsid, in which the nucleocapsid capsule is situated at the surface membrane, but may also be used in the case of adenoviridae, poxviridae and coronaviridae, such as, especially, human corona viruses.

The compounds of the formula I are used especially in the case of herpesviridae, picornaviridae and myxo viruses, but may also be used in the case of mastadeno viruses, such as, especially, human adeno viruses, in the case of chordopoxvirinae, such as, chiefly, orthopox viruses, such as, especially, for example, vaccinia viruses, in the case of reoviridae, principally (especially human) rota viruses, and in the case of caliciviridae and rhabdoviridae, such as, especially, vesiculo viruses in humans and also in horses, cattle and pigs.

The compounds of the formula I are used chiefly in the case of alpha-herpesvirinae, such as varicella viruses, for example human varicella-zoster viruses, rhino viruses, cardio viruses and ortho-myxoviridae, but may also be used in the case of beta-herpesvirinae, such as especially human cytomegalo viruses, in the case of aphtho viruses, especially aphtho viruses in cloven-hoofed animals, such as, especially, cattle, and in the case of para-myxoviridae, such as, especially, pneumo viruses, for example respiratory syncytial viruses in humans, and such as, also, morbilli viruses or para-myxo viruses, such as para-influenza viruses, for example human para-influenza viruses, including Sendai viruses, and in the case of arbo viruses or vesiculo viruses, for example *Vesicular stomatitis* viruses.

The compounds of the formula I are used more especially in the case of simplex viruses, for example human Herpes simplex viruses of types 1 and 2, in the case of human encephalomyocarditis viruses, in the case of influenza viruses, such as, especially, influenza A and influenza B viruses, in the case of vaccinia and para-influenza viruses and most especially in the case of the viruses mentioned in the Examples.

The compounds of the formula I can be used for the prophylaxis and therapy of virus infections, especially of warm-blooded animals, including humans, by being administered enterally or parenterally, especially together with suitable adjuncts or carrier materials. They are preferably applied to the mucous membranes, for example intranasally, rectally, vaginally or to the conjunctiva of the eye, or orally. The antiviral effect occurs, however, also upon administration by other routes, for example subcutaneously, intravenously, intramuscularly or upon application to the normal skin.

The dosage of the active ingredient depends, inter alia, on the species of warm-blooded animal, the organism's state of defence, the mode of administration and the type of virus. There is relatively little relationship between dosage and effect.

For prevention, a single dose of from approximately 0.01 mg to approximately 25 mg, preferably from 0.05 to 7 mg, for example 0.5 mg, of active ingredient is administered to a warm-blooded animal of approximately 70 kg body weight, for example a human. The prophylactic effect of that dose lasts for several weeks. If required, for example when there is increased risk of infection, the administration of that dose may be repeated.

The therapeutic dose for warm-blooded animals of approximately 70 kg body weight is from 0.1 mg to 25 mg, preferably from 1 to 10 mg, for example 5 mg, especially in the case of oral administration. The dosage in the case of topical, especially intranasal, administration is up to 10 times lower. If necessary, the administration of compounds of the formula I can be repeated until there is an improvement in the illness. A single administration is often sufficient, however.

The invention thus relates also to a method for the prophylaxis or therapy of virus infections in warm-blooded animals, comprising the administration to a warm-blooded animal of an amount of a compound of the formula I or a pharmaceutically acceptable salt thereof that is effective for the prophylaxis or therapy of virus infections.

The compounds of the formula I and their pharmaceutically acceptable salts inhibit the action of phospholipase $A_2$ from human granulocytes ($IC_{50}$ between approximately 0.1 μmol/liter and 10 μmol/liter). Phospholipase $A_2$ directly inhibits the release of mediators of inflammatory processes, for example of arachidonic acid. The compounds according to the invention can therefore be used also as anti-allergic or anti-inflammatory agents.

Preferred are the above-mentioned compounds of the formula I in which $R^3$ represents hydrogen and $R^4$ represents 1,2-dihydroxy-ethyl in which either only the 2-hydroxy group or both hydroxy groups independently of each other are esterified by a $C_{10-24}$-alkanoic acid or by a $C_{18}$-alkenoic acid, or $R^3$ and $R^4$ each represents hydroxymethyl esterified by a $C_{10-24}$-alkanoic acid or a $C_{18}$-alkenoic acid, and their salts.

There are preferred, especially, the abovementioned compounds of the formula I in which $R^3$ represents hydrogen and $R^4$ represents 1,2-dihydroxyethyl in which both hydroxy groups independently of each other are esterified by a $C_{10-24}$-alkanoic acid or a $C_{18}$-alkenoic acid, or $R^3$ and $R^4$ each represents hydroxymethyl esterified by a $C_{10-24}$-alkanoic acid or a $C_{18}$-alkenoic acid, and their salts.

More especially preferred are the above-mentioned compounds of the formula I in which $R^3$ represents hydrogen and $R^4$ represents 1,2-dihydroxyethyl in which both hydroxy groups independently of each other are esterified by an unbranched $C_{10-24}$-alkanoic acid having an even number of carbon atoms or by an unbranched $C_{18}$-alkenoic acid having from 1 to 3 isolated double bonds, or $R^3$ and $R^4$ each represents hydroxymethyl esterified by an unbranched $C_{10-24}$-alkanoic acid having an even number of carbon atoms or by an unbranched $C_{18}$-alkenoic acid having from 1 to 3 isolated double bonds, and their salts.

More especially preferred are also the abovementioned compounds of the formula I in which Y represents unbranched $C_1$-$C_5$-alkylene or the radical —CH$_2$—CH$_2$—CH$_2$—CO—NH—CH$_2$—, and their salts.

More especially preferred are, in particular, the compounds of the formula I in which $R^1$ represents (a) D-aldohexosyl that may be glycosidically linked in the 4-position to D-aldohexosyl, (b) 6-deoxy-aldohexosyl or (c) 2-acetylamino-2-deoxy-D-aldohexosyl, it being possible for free hydroxy groups present in the radicals mentioned under (a) to (c) above to be peracetylated, X represents oxygen or sulphur, Y represents $C_{3-5}$-alkylene in which a non-terminal methylene group may be replaced by carbonylimino, $R^2$ represents hydrogen or carboxy, $R^3$ represents hydrogen and $R^4$ represents 1,2-dihydroxyethyl in which either only the 2-hydroxy group or both hydroxy groups independently of each other are esterified by an unbranched $C_{10-24}$-alkanoic acid or by an unbranched $C_{18}$-alkenoic acid, or $R^3$ and $R^4$ each represents hydroxymethyl esterified by an unbranched $C_{10-24}$-alkanoic acid or by an unbranched $C_{18}$-alkenoic acid having from 1 to 3 isolated double bonds, and their salts.

More especially preferred are, in particular, also the compounds of the formula I in which $R^1$ represents (a) D-aldohexosyl in which free hydroxy groups may be peracetylated, (b) D-aldohexosyl that is glycosidically linked in the 4-position to D-aldohexosyl, (c) 6-deoxvaldohexosyl or, (d) 2-acetylamino-2-deoxy-D-aldohexosyl, X represents oxygen or sulphur, Y represents alkylene having up to 5 carbon atoms in which a non-terminal methylene group may be replaced by carbonylimino, $R^2$ represents hydrogen or carboxy, $R^3$ represents hydrogen and $R^4$ represents 1,2-dihydroxyethyl in which both hydroxy groups are esterified by an unbranched $C_{10-20}$-alkanoic acid having an even number of carbon atoms or by oleic acid, or $R^3$ and $R^4$ each represents hydroxymethyl esterified by an unbranched $C_{10-20}$-alkanoic acid having an even number of carbon atoms or by oleic acid, and their salts.

Especially preferred are the above-mentioned compounds of the formula I in which $R^1$ represents D-glucosyl, 2,3,4,6-tetra-O-acetyl-D-glucosyl, D-mannosyl, 2,3,4,6-tetra-O-acetyl-D-mannosyl, D-galactosyl, D-cellobiosyl, D-lactosyl, D-maltosyl, L-fucosyl or 2-acetylamino-2-deoxy-D-glucosyl, and their salts.

Especially preferred are also the compounds of the formula I in which $R^1$ represents 2,3,4,6-tetra-O-acetyl-β-D-glucopyranosyl, β-D-glucopyranosyl, 2,3,4,6-tetra-O-acetyl-α-D-mannopyranosyl, β-D-galactopyranosyl, β-D-cellobiopyranosyl, β-D-lactopyranosyl, β-D-maltopyranosyl, β-L-fucopyranosyl, 2-acetylamino-2-deoxy-β-D-glucopyranosyl or β-D-mannopyranosyl, X represents oxygen or sulphur, Y represents trimethylene, methylene or —CH$_2$—CH$_2$—CH$_2$—CON-H—CH$_2$—, $R^2$ represents hydrogen or carboxy, $R^3$ represents hydrogen and $R^4$ represents 1,2-dilauroyloxy-ethyl, 1,2-dimyristoyloxy-ethyl, 1,2-di-palmitoyloxy-ethyl, 1,2-distearoyloxy-ethyl, 1,2-n-eicosanoyloxy-ethyl, 1,2-dioleoyloxy-ethyl, n-decanoyloxy-methyl or 2-palmitoyloxy-ethyl, or $R^3$ and $R^4$ each represents lauroyloxy-methyl, and their pharmaceutically acceptable salts.

Most especially preferred are the above-mentioned compounds of the formula I in which $R^2$ represents hydrogen and/or in which Y represents trimethylene or the radical —CH$_2$—CH$_2$—CH$_2$—CO—NH—CH$_2$—and/or in which $R^3$ represents hydrogen and $R^4$ represents 1,2-dipalmitoyloxy-ethyl, or $R^3$ and $R^4$ each represents lauroyloxymethyl, and their salts.

In the first place there are preferred the pharmaceutically acceptable salts of the above-mentioned compounds of the formula I.

Above all there are preferred the compounds of the formula I described in the Examples and/or their pharmaceutically acceptable salts.

The compounds of the formula I are manufactured in a manner known per se, for example by (a) reacting a compound of the formula II $$R^1\text{-}X^1 \qquad\qquad (II)$$

in which $R^1$ has the meaning mentioned above and $X^1$ represents the group X-H in which X has the meaning mentioned above or represents a nucleophilic leaving group, an free functional groups present in this compound, with the exception of the group participating in the reaction, being, if necessary, protected by readily removable protecting groups, or a reactive derivative thereof, with a compound of the formula III

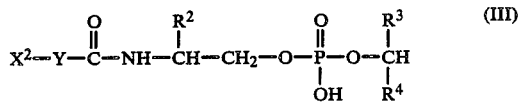 (III)

in which X² represents the group H-X in which X has the meaning mentioned above or represents a nucleophilic leaving group, and the other substituents have the meanings mentioned above, any free functional groups present in this compound, with the exception of the group participating in the reaction, being, if necessary, protected by readily removable protecting groups, and removing any protecting groups present, or (b) reacting a carboxylic acid of the formula IV

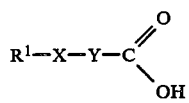 (IV)

in which the substituents have the meanings mentioned above, any free functional groups present in this compound, with the exception of the group participating in the reaction, being, if necessary, protected by readily removable protecting groups, or a reactive carboxylic acid derivative thereof, with an amino compound of the formula V

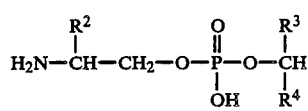 (V)

in which the substituents have the meanings mentioned above, any free functional groups present in this compound, with the exception of the group participating in the reaction, being, if necessary, protected by readily removable protecting groups, or with a reactive derivative thereof, and removing any protecting groups present, or (c) for the manufacture of a compound of the formula I in which Y represents alkylene in which a non-terminal methylene group has been replaced by carbonylimino, reacting a compound of the formula VI

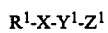 (VI)

in which Y¹ represents alkylene and Z¹ represents carboxy or amino and the other substituents have the meanings mentioned above, any free functional groups present in this compound, with the exception of the group participating in the reaction, being, if necessary, protected by readily removable protecting groups, or a reactive derivative thereof, with a compound of the formula VII

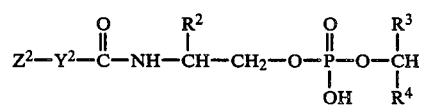 (VII)

in which Z² represents amino if Z¹ in the reactant of the formula VI represents carboxy, or in which Z² represents carboxy if Z¹ in the reactant of the formula VI represents amino, and in which Y² represents alkylene, with the proviso that the radical —Y¹—CONH—Y²— or —Y¹—NHCO—Y²— corresponds to the radical Y, and the other substituents have the meanings mentioned above, any free functional groups present in this compound, with the exception of the group participating in the reaction, being, if necessary, protected by readily removable protecting groups, or with a reactive derivative thereof, and removing any protecting groups present, or (d) reacting a compound of the formula VIII

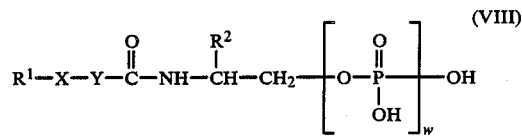 (VIII)

in which w represents 0 or 1 and the substituents have the meanings mentioned above, any free functional groups present in this compound, with the exception of the group participating in the reaction, being, if necessary protected by readily removable protecting groups, or a reactive derivative thereof, with a compound of the formula IX

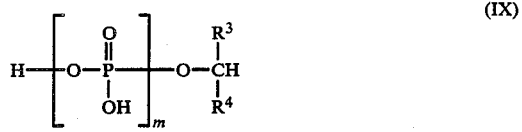 (IX)

in which m represents 1 if w in the reactant of the formula VIII represents 0, or in which m represents 0 if w in the reactant of the formula VIII represents 1, and the substituents have the meanings mentioned above, any free functional groups present in this compound, with the exception of the group participating in the reaction, being, if necessary, protected by readily removable protecting groups, or with a reactive derivative thereof, and removing any protecting groups present, or (e) oxidising a compound of the formula X

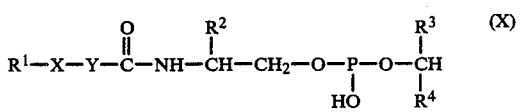 (X)

in which the substituents have the meanings mentioned above, any free functional groups present in this compound, with the exception of the group participating in the reaction, being, if necessary, protected by readily removable protecting groups, or a tautomeric compound, with a suitable oxidising agent and removing any protecting groups present, or (f) hydrolysing a compound of the formula XI

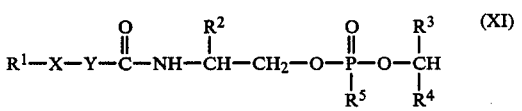 (XI)

in which R⁵ represents halogen or another readily hydrolysable group and the other substituents have the meanings mentioned above, any free functional groups present in this compound, with the exception of the group participating in the reaction, being, if necessary, protected by readily removable protecting groups, and removing any protecting groups present, or (g) esterifying a compound of the formula XII

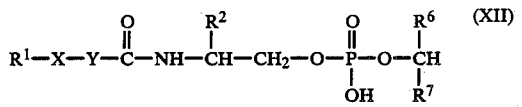

in which $R^6$ represents hydrogen and $R^7$ represents 1,2-dihydroxyethyl, 2-hydroxy-ethyl, hydroxymethyl or 1,2-dihydroxy-ethyl in which one of the two hydroxy group is esterified by an unsubstituted aliphatic $C_{2\text{-}24}$-carboxylic acid, or $R^6$ represents hydroxymethyl and $R^7$ represents hydroxymethyl or hydroxymethyl that is esterified by an unsubstituted aliphatic $C_{10\text{-}24}$-carboxylic acid, and the other substituents have the meanings mentioned above, any free functional groups present in this compound, with the exception of the group participating in the reaction, being, if necessary, protected by readily removable protecting groups, with an unsubstituted aliphatic $C_{10\text{-}24}$carboxylic acid or with a reactive acid derivative thereof, and removing any protecting groups present, or (h) removing the protecting group(s) that is (are) not contained in the desired end product of the formula I from a compound of the formula XIII

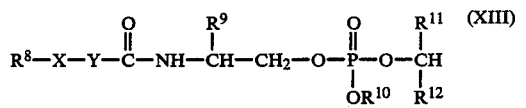

in which $R^8$ represents aldohexosyl or D-aldohexosyl that is glycosidically linked in the 4- or the 6-position to D-aldohexosyl, aldopentosyl, 6-deoxyaldohexosyl or 2-acetylamino-2-deoxy-D-aldohexosyl, at least one hydroxy group in the above-mentioned radicals being protected by a readily removable protecting group, or $R^8$ has the meaning of $R^1$, X and Y have the meanings mentioned above, $R^9$ represents carboxy protected by a readily removable protecting group or has the meaning of $R^2$, $R^{10}$ represents hydrogen or a readily removable phosphoric acid-protecting group, $R^{11}$ represents hydrogen and $R^{12}$ represents a 1,2-dihydroxy-ethyl group in which one hydroxy group is protected by a readily removable protecting group and unsubstituted aliphatic $C_{10\text{-}24}$-carboxylic acid or $R^{12}$ has the meaning of $R^4$, with the proviso that, in a compound of the formula XIII, at least one readily removable protecting group is present that is not contained in the desired end product of the formula I, and, after carrying out one of the above-mentioned processes (a)–(h), for the manufacture of a salt, if necessary, a compound of the formula I is converted into one of its salts.

The processes mentioned above are explained in detail below:

It is preferable to manufacture the compounds of the formula I according to process (b) or (c). Process (h) also can be carried out easily. Also easy to carry out are processes (e), (f) and (g), but the starting materials required for these are not always easily accessible.

Process (a)

A nucleophilic leaving group $X^1$ or $X^2$ is especially a halide having an atomic weight of between 35 and 127, that is to say a chloride, bromide or iodide. A reactive derivative of a compound of the formula II is, for example, an isothiuronium salt, that is to say $X^1$ represents $-S-C(-NH_2)=\oplus$, the ion of opposite charge being, for example, one of the halides mentioned above.

The reaction is preferably carried out by reacting a compound of the formula II in which $X^1$ represents one of the halides mentioned above, for example bromide or iodide, with a compound of the formula III, or a suitable salt, for example a silver salt, thereof, in which $X^2$ represents the group HX. Compounds of the formula I in which X represents sulphur are preferably manufactured by reacting an isothiuronium salt of a compound of the formula II with a compound of the formula III in which $X^2$ represents a nucleophilic leaving group, for example iodide.

If necessary, free hydroxy groups in the radical(s) $R^1$ and/or $R^4$, free carboxy $R^2$ and/or the phosphoric acid group are protected by readily removable protecting groups. Suitable protecting groups and their removal are described in process (b).

The starting materials are known or may be manufactured according to processes that are known per se, for example analogously to suitable processes described in this Application.

Process (b)

Process (b) is preferably carried out by reacting a reactive carboxylic acid derivative of a compound of the formula IV with a compound of the formula V in which the amino group is in free form. During the reaction, the activation of the carboxylic acid IV is preferably effected in situ, for example with 1-hydroxy-benzotriazole/dicyclohexyl carbodiimide, since then it is possible to dispense with the protection of functional groups in the compounds IV and V provided that $R^2$ represents hydrogen.

If desired, free hydroxy $R^2$ and, if necessary, free hydroxy in the radicals $R^1$ and $R^4$ and also the phosphoric acid group are protected by readily removable protecting groups.

Protecting groups and the methods by which they are introduced and removed are described, for example, in "Protective Groups in Organic Chemistry", Plenum Press, London, New York 1973, and in "Methoden der organischen Chemie", Houben-Weyl, 4th edition, vol. 15/1, Georg-Thieme-Verlag, Stuttgart 1974 and in Theodora W. Greene, "Protective Groups in Organic Synthesis", John Wiley & Sons, New York 1981. It is characteristic of such protecting groups that they can be removed readily, that is to say without undesired secondary reactions taking place, for example by solvolysis, reduction, photolysis or also under physiological conditions.

Hydroxy-protecting groups are, for example, acyl radicals, such as lower alkanoyl optionally substituted, for example, by halogen, such as 2,2-dichloroacetyl, or acyl radicals of carbonic acid semiesters, especially tert.-butoxycarbonyl, optionally substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, also readily removable etherifying groups, such as tert.-lower alkyl, for example tert.-butyl, 2-oxa- or 2-thia-aliphatic or 2-oxa- or 2-thia-cycloaliphatic hydrocarbon radicals, especially 1-lower alkoxy-lower alkyl or 1-lower alkylthio-lower alkyl, for example methoxymethyl, 1-methoxy-ethyl, 1-ethoxy-ethyl, methylthiomethyl, 1-methylthio-ethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, suitable substituents of the phenyl radicals being, for example, halogen, such as chlorine, lower alkoxy, such as methoxy and/or nitro.

Carboxy groups are customarily protected in esterified form, such ester groupings being readily removable under mild conditions. Carboxy groups protected in this manner contain as esterifying groups especially lower alkyl groups that are branched in the 1-position or suitably substituted in the 1- or 2-position. Preferred carboxy groups in esterified form are, inter alia, tert.-lower alkoxycarbonyl, for example tert.-butoxycarbonyl, arylmethoxycarbonyl having one or two aryl radicals, these being phenyl radicals that are optionally mono- or polysubstituted, for example, by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example, as mentioned above, for example 4-methoxybenzyloxycarbonyl, or 4-nitrobenzyloxycarbonyl, or diphenylmethoxycarbonyl optionally substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group is benzoyl that is optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is optionally substituted, for example, by lower alkyl, lower alkoxy, aryl, halogen and/or by nitro, such as corresponding, optionally substituted lower alkyl, phenyl-lower alkyl, cycloalkyl or phenyl, for example 2-trilower alkylsilylethoxycarbonyl, 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

The organic silyl or stannyl radicals mentioned hereinbefore and hereinafter preferably contain lower alkyl, especially methyl, as substituents of the silicon or tin atoms. Corresponding silyl or stannyl groups are especially tri-lower alkylsilyl, especially trimethylsilyl, also dimethyl-tert.-butyl-silyl, or correspondingly substituted stannyl, for example tri-n-butylstannyl.

Preferred protected carboxy groups are tert.-lower alkoxycarbonyl, such as tert.-butoxycarbonyl, and especially benzyloxycarbonyl that is optionally substituted, for example, as mentioned above, such as 4-nitrobenzyloxycarbonyl, or diphenylmethoxycarbonyl, above all 2-(trimethylsilyl)-ethoxycarbonyl.

The phosphoric acid group is protected, for example, in the form of the methyl, phenyl, 2-chlorophenyl, 2,5-dichloro-phenyl, 4-nitro-phenyl, benzyl, 2-(4-nitrophenyl)-ethyl or 2-cyano-ethyl ester.

Reactive carboxylic acid derivatives are especially reactive activated esters or reactive anhydrides, also reactive cyclic amides.

Activated esters of acids are especially esters that are unsaturated at the linking carbon atom of the esterifying radical, for example of the vinyl ester type, such as true vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexyl carbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (obtainable, for example, by treatment of the corresponding acid with chloroacetonitrile in the presence of a base; cyanomethyl esters method), thio esters, especially phenylthio esters optionally substituted, for example, by nitro (obtainable, for example, by treatment of the corresponding acid with thiophenols that are optionally substituted, for example, by nitro, inter alia with the aid of the anhydride or carbodiimidemethod; activated thio esters method), or amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, or 1-hydroxybenzotriazole, for example according to the anhydride or carbodiimide method; activated N-hydroxyesters method).

Anhydrides of acids may be symmetric or preferably mixed anhydrides of these acids, for example anhydrides with inorganic acids, such as acid halides, especially acid chlorides (obtainable, for example, by treating the corresponding acid with thionyl chloride, phosphorus pentachloride or oxalyl chloride; acid chloride method), azides (obtainable, for example, from a corresponding acid ester by way of the corresponding hydrazide and the treatment of the latter with nitrous acid; azide method), anhydrides with carbonic acid semi-derivatives, such as corresponding esters, for example carbonic acid lower alkyl semi-esters (obtainable, for example, by treating the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (obtainable, for example, by treating the corresponding acid with phosphorus oxychloride; phosphorus oxychloride method), or anhydrides with organic acids, such as mixed anhydrides with organic carboxylic acids (obtainable, for example, by treating the corresponding acid with an optionally substituted lower alkanecarboxylic acid halide or phenyl-alkanecarboxylic acid halide, for example phenylacetic acid chloride, pivalic acid chloride or trifluoroacetic acid chloride; mixed carboxylic acid anhydrides method) or with organic sulphonic acids (obtainable, for example, by treating a salt, such as an alkali metal salt, of the corresponding acid with a suitable organic sulphonic acid halide, such as a lower alkanesulphonic acid chloride or arylsulphonic acid chloride, for example methane- or p-toluene-sulphonic acid chloride; mixed sulphonic acid anhydrides method), and symmetric anhydrides (obtainable, for example, by condensing the corresponding acid in the presence of a carbodiimide or of 1-diethylaminopropyne; symmetric anhydrides method).

Suitable cyclic amides are especially amides having five-membered diazacycles of aromatic character, such as amides with imidazoles, for example imidazole (obtainable, for example, by treating the corresponding acid with N,N'-carbonyldiimidazole; imidazolide method), or pyrazoles, for example 3,5-dimethylpyrazole (obtainable, for example, by way of the acid hydrazide by treatment with acetylacetone; pyrazolide method).

As mentioned, derivatives of acids that are used as acylating agents may also be formed in situ. For example, N,N'-disubstituted amidino esters can be formed in situ by reacting a mixture of the amino compound and the acid used as acylating agent in the presence of a suitable N,N-disubstituted carbodiimide, for example N,N'-dicyclohexyl carbodiimide. Amino or amido esters of the acids used as acylating agents may also be formed in the presence of the starting material that is to be acylated, by reacting a mixture of the corresponding acid and amino starting materials in the presence of an N,N'-disubstituted carbodiimide, for example N,N'-dicyclohexyl carbodiimide, and of an N-hydroxyamine or N-hydroxyamide, for example N-hydroxysuccinimide, optionally in the presence of a suitable base, for example 4-dimethylaminopyridine.

The reaction can be carried out in a manner known per se, the reaction conditions depending primarily on whether and in which manner the carboxy group of the acylating agent has been activated, customarily in the presence of a suitable solvent or diluent or a mixture thereof, and, if necessary, in the presence of a condensation agent which, for example, if the carboxy group participating in the reaction is in the form of an anhydride, may also be an acid-binding agent, while cooling or heating, for example in a temperature range of from approximately −30° C. to approximately +150° C., especially approximately from 0° C. to +100° C., preferably from room temperature (approximately +20° C.) to +70° C., chiefly between room temperature and +40° C., in a closed reaction vessel and/or in the atmosphere of an inert gas, for example nitrogen. Customary condensation agents are, for example, carbodiimides, for example N,N'-diethyl, N,N'-dipropyl, N,N'-dicyclohexyl or N-ethyl-N'-(3-dimethylaminopropyl) carbodiimide, suitable carbonyl compounds, for example carbonyldiimidazole, or 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline. Customary acid-binding condensation agents are, for example, alkali metal carbonates or bicarbonates, for example sodium or potassium carbonate or bicarbonate (customarily together with a sulphate), or organic bases, such as customarily sterically hindered tri-lower alkylamines, for example N,N-diisopropyl-N-ethyl-amine.

The removal of the protecting groups, for example the carboxy- or hydroxy-protecting groups, that are not constituents of the desired end product of the formula I is effected in a manner known per se, optionally in stages or simultaneously, for example by means of solvolysis, especially hydrolysis, alcoholysis or acidolysis, or by means of reduction, especially hydrogenolysis or chemical reduction, it being possible also to use enzymatic methods.

For example, tert.-lower alkoxycarbonyl or lower alkoxycarbonyl substituted in the 2-position by an organic silyl group or in the 1-position by lower alkoxy or lower alkylthio, or optionally substituted diphenylmethoxycarbonyl, can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Suitably substituted benzyloxycarbonyl, such as 4-nitrobenzyloxycarbonyl, can also be converted into free carboxy by chemical reduction, for example by treatment with an alkali metal dithionite, for example sodium dithionite, or with a reducing metal, for example zinc, or a reducing metal salt, such as a chromium-(II) salt, for example chromium(II) chloride, customarily in the presence of a hydrogen-yielding agent that together with the metal is capable of producing nascent hydrogen, such as an acid, especially a suitable carboxylic acid, such as an optionally substituted, for example hydroxysubstituted, lower alkanecarboxylic acid, for example acetic acid, formic acid, glycolic acid, diphenylglycolic acid, lactic acid, mandelic acid, 4-chloromandelic acid or tartaric acid, or an alcohol or thiol, it being preferable to add water. It is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy by treatment with a reducing metal or a reducing metal salt, as described above. Aroylmethoxycarbonyl can also be cleaved by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide.

A hydroxy group protected by a suitable acyl group, an organic silyl group or by an optionally substituted 1-phenyl-lower alkyl is freed by solvolysis or reduction depending on the nature of the protecting group. Hydroxy protected by optionally substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, while a hydroxy group etherified by tert.-lower alkyl or by a 2-oxa- or 2-thia-aliphatic or a 2-oxa- or 2-thia-cycloaliphatic hydrocarbon radical is freed by acidolysis, for example by treatment with a mineral acid or a strong carboxylic acid, for example trifluoroacetic acid. Two hydroxy groups that are protected together by means of a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid. Hydroxy etherified by an organic silyl radical, for example trimethylsilyl, can also be freed with a salt of hydrofluoric acid yielding fluoride anions, for example tetrabutylammonium fluoride.

A phosphoric acid group protected in the form of the methyl ester can be freed, for example, with a suitable lithium halide, preferably lithium bromide, in a solvent, such as, for example, acetone. A phosphoric acid group protected in the form of the benzyl ester can be freed, for example, by hydrogenolysis in the presence of palladium-on-carbon catalysts. Phenyl esters are cleaved with hydrogen in the presence of platinum catalysts or mixed platinum/palladium catalysts. A phosphoric acid group protected in the form of the 2-chlorophenyl, 2,5-dichlorophenyl or 4-nitrophenyl ester is freed by oximate cleavage, for example by means of the N,N'-tetramethylguanidinium salt of 2-nitrobenzaldoxime, 4-nitrobenzaldoxime or 2-pyridinealdoxime. The 2-(4-nitrophenyl)-ethyl protecting group is removed by β-elimination by means of DBU (1,8-diazabicyclo[5.4.-0]undec-7-ene) in an aprotic solvent and the 2-cyanoethyl protecting group by β-elimination by means of triethylamine/water.

Preferably, when several protected functional groups are present-, the protecting groups are so chosen that more than one such group can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium-on-carbon catalyst. If the desired end products contain protecting groups, for example if $R^2$ represents benzyloxycarbonyl, the protecting group that are to be removed when the reaction has taken place are so chosen that they may be removed again region selectively: for example, hydroxy in the radical $R^1$ or $R^4$ that is etherified by an organic silyl radical can be freed with fluoride whilst a benzyl protecting group in the radical $R^2$ is retained.

Process (c)

Process (c) is carried out analogously to Process (b).

Process (d)

Preferably, a compound of the formula VIII in which w represents 0 is reacted with a compound of the formula IX in which m represents 1, or especially with a reactive derivative of such a compound of the formula IX.

A reactive derivative of a compound of the formula VIII in which w represents 1, or a compound of the formula IX in which m represents 1 is, for example, a mono- or bis-anhydride with a strong acid, especially a mineral acid, such as, especially, a hydrohalic acid, such as, chiefly, hydrochloric acid. The second acidic phosphoric acid group may be present in that form or in the form of an anhydride as described above or in protected form. Reactive phosphoric acid derivatives are, for example, also benzo-1,2,3-triazol-1-yl esters, N-succinimidyl esters and 1,2,4-triazolides.

The formation of reactive phosphoric acid derivatives can also be effected in situ in the presence of compounds that are able to form with phosphoric acid or monoesters thereof at least intermediately reactive compounds of anhydride- or enol ester-like character, for example in the presence of p-toluenesulphonic acid chloride, cyanuric chloride, N-alkyl-5-phenylisoxazolium salts, ethoxyacetylene or, preferably, trichloroacetonitrile or especially a carbodiimide, such as chiefly dicyclohexyl carbodiimide. For example, a phosphoric acid monoester of the formula VIII or IX in which w or m, respectively, represents 1 can be reacted with excess alcohol of the formula IX or VIII, respectively, in which m or w, respectively, represents 0, in the presence of several times, for example five times, the molar amount of dicyclohexyl carbodiimide in the presence or absence of a tertiary amine.

If both acidic groups in a phosphoric acid monoester are in the form of an anhydride with a hydrohalic acid, it is possible to obtain, in the first instance, in addition to the triester, also phosphoric acid diester halides which then have to be hydrolysed to diesters by means of water, water-yielding agents or by heating with tertiary alcohols, such as tert.-butanol or tetrahydropyranol [see Process (f)].

If a phosphoric acid monoester dihalide, for example a phosphoric acid monoester dichloride, is used as starting material, the reaction is preferably carried out in the presence of a tertiary amine, such as pyridine, lutidine or quinoline, an additional activation of the ester chloride being effected by dimethylformamide.

A preferred form of Process (d) is the reaction of a phosphoric acid monoester dichloride with the corresponding alcohol in the presence of a tertiary amine, followed by the hydrolysis of the phosphoric acid diester halide which is initially obtained.

In a reactive derivative of a compound of the formula VIII or IX in which w or m, respectively, represents 0, the hydroxy group participating in the reaction is in reactive, esterified form.

Reactive esterified hydroxy is, for example, hydroxy esterified by a strong inorganic or organic acid, such as hydroxy esterified by a mineral acid, for example a hydrohalic acid, such as hydrochloric acid, hydrobromic acid or hydriodic acid, also sulphuric acid, or a halosulphuric acid, for example fluorosulphuric acid, or with a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic acid, trifluoromethanesulphonic acid or p-toluenesulphonic acid, preferably a chloride, bromide or iodide.

The reaction can be carried out by reacting a reactive phosphoric acid derivative of the formula VIII or IX with an alcohol of the formula IX or VIII, respectively, that is in non-activated form, or by reacting a reactive esterified alcohol of the formula VIII or IX with a phosphoric acid derivative of the formula IX or VIII, respectively, that is in non-activated form, or with a reactive salt thereof.

With a view to the intended nucleophilic substitution reaction, especially reactive salts are used as salts of compounds of the formula VIII or IX, for example salts, such as silver salts, that are capable of forming with the nucleophilic leaving group in the reactant, for example one of the above-mentioned halide ions, a sparingly soluble precipitate, or salts having a large cation, for example caesium salts, in which the nucleophilic nature of the phosphate radical is increased. To increase the nucleophilic nature of the phosphate radical, the ion of opposite charge also may be spatially removed, for example by the addition of complex formers, such as Crown ethers, for example 18-Crown-6. When using 18-Crown-6, the reaction can be carried out with a potassium salt.

A preferred form of Process (d) is the reaction of the silver salt of a phosphoric acid monoester of the formula VIII or IX in which one of the two acid groups has been protected by a readily removable protecting group, with a reactive alcohol of the formula IX or VIII, respectively, in which the OH group has been replaced by chlorine, bromine or, preferably, iodine.

Suitable protecting groups and their removal are described in Process (b).

Process (e)

The compounds of the formula X are predominantly in the tautomeric form in which a proton is bonded directly to phosphorus. The oxidation can be carried out, for example, with aqueous potassium permanganate at temperatures of around 0° C. In an aqueous medium, alkali metal iodates, periodates and hypochlorites, peracetic acid, N-chloro-4-methyl-benzene-sulphonic acid amide, inter alia, are suitable as oxidising agents.

Suitable protecting groups and their removal are described in process (b).

Process (f)

Halogen $R^5$ is bromine or iodine, but above all chlorine.

Readily hydrolysable groups other than halogen are, for example, benzo-1,2,3-triazol-1-yloxy, N-succinimidyloxy and 1,2,4-triazol-1-yl.

The hydrolysis is carried out with water or a water-yielding agent, preferably at elevated temperature, for example from 30° to 95° C.

The starting materials can be obtained, for example, as described in Process (d) or by chlorination of the corresponding phosphorous acid diesters, for example with elemental chlorine.

Suitable protecting groups and their removal are described in Process (b).

Process (g)

In a compound of the formula XII, free hydroxy groups in the radical $R^1$ must be protected. If desired, free carboxy $R^2$ and/or the phosphoric acid group also may be protected. Suitable protecting groups and their removal are described in Process (b).

Reactive derivatives of the unsubstituted aliphatic carboxylic acid are analogous to those described in Process (b), it being possible for the activation to be effected also in situ, that is to say in the presence of the compound XIII.

The reaction is carried out analogously to Process (b).

The starting material of the formula XII can be obtained, for example, analogously to Process (b) if, instead of compounds of the formula V, compounds are used in which at least one hydroxy group in the radicals $R^3$ and $R^4$ is protected by a readily removable group and these protecting groups are removed after reaction with the carboxylic acid IV has taken place. Alternatively, a starting compound of the formula XII in which $R^3$ represents hydrogen and $R^4$ represents 1,2-dihydroxyethyl in which the 2-hydroxy group is esterified by an unsubstituted aliphatic $C_{10-24}$-carboxylic acid can be manufactured also by reacting a compound of the formula I in which $R^3$ represents hydrogen and $R^4$ represents 1,2-dihydroxy-ethyl in which the 2-hydroxy group is esterified by an unsubstituted aliphatic $C_{10-24}$-carboxylic acid and the 1-hydroxy group is esterified by an unsubstituted aliphatic $C_{2-24}$-carboxylic acid, with an enzyme that is suitable for the regioselective removal of the radical esterifying the 1-hydroxy group. A suitable enzyme is, for example, phospholipase $A_2$ which is commercially available (for example Boehringer AG, Mannheim, Federal Republic of Germany).

Process (h)

Suitable protecting groups and their removal are described in Process (b).

Additional operations

For the manufacture of a compound of the formula I in which $R^2$ represents lower alkoxycarbonyl, benzyloxycarbonyl or carbamoyl, a compound of the formula I in which $R^2$ represents carboxy, any free functional groups present in this compound, with the exception of the group participating in the reaction, being, if necessary, protected by readily removable protecting groups, or a reactive acid derivative thereof, can be esterified or amidated. The esterification or amidation can be carried out by reacting a reactive acid derivative with the corresponding lower alkanol or with benzyl alcohol or ammonia. The reactive acid derivatives are analogous to those described in Process (b). Preferably, however, the esterification is carried out by reacting a compound of the formula I in which $R^2$ represents non-activated carboxy with a reactive esterifying agent. Suitable agents for the esterification are, for example, corresponding diazo compounds, such as optionally substituted diazo-lower alkanes, for example diazomethane, diazoethane or diazo-n-butane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating slightly, and also, if necessary, in a closed vessel and/or under an inert gas atmosphere, for example a nitrogen atmosphere.

Other suitable agents for the esterification are esters of corresponding alcohols, especially those with strong inorganic or organic acids, such as mineral acids, for example hydrohalic acids, such as hydrochloric, hydrobromic or hydriodic acid, also sulphuric acid, or halosulphuric acids, for example fluorosulphuric acid, or with strong organic sulphonic acids, such as lower alkanesulphonic acids optionally substituted, for example, by halogen, such as fluorine, or aromatic sulphonic acids, such as, for example, benzenesulphonic acids optionally substituted by lower alkyl, such as methyl, halogen, such as bromine, and/or by nitro, for example methanesulphonic, trifluoromethanesulphonic or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are customarily used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. There are preferably used suitable condensation agents, such as alkali metal carbonates or bicarbonates, for example sodium or potassium carbonate or bicarbonate (customarily together with a sulphate), or organic bases, such as customarily sterically hindered trilower alkylamines, for example N,N-diisopropyl-N-ethylamine (preferably together with halosulphonic acid lower alkyl esters or optionally halo-substituted methanesulphonic acid lower alkyl esters), the reaction being carried out while cooling, at room temperature or while heating, for example at temperatures of from approximately $-20°$ C. to approximately 50° C. and, if necessary, in a closed vessel and/or in an inert gas atmosphere, for example a nitrogen atmosphere.

Other agents for the esterification are corresponding trisubstituted oxonium salts (so-called Meerwein salts), or disubstituted carbenium or halonium salts in which the substituents are the etherifying radicals, for example tri-lower alkyloxonium salts, and di-lower alkoxycarbenium or di-lower alkylhalonium salts, especially the corresponding salts with complex, fluorine-containing acids, such as the corresponding tetrafluoroborates, hexafluorophosphates, hexafluoroantimonates, or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These agents are preferably used in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered tri-lower alkylamine, for example N,N-diisopropyl-N-ethyl-amine, and while cooling, at room temperature or while heating slightly, for example at from approximately $-20°$ C. to approximately 50° C., if necessary in a closed vessel and/or in an inert gas atmosphere, for example a nitrogen atmosphere.

A preferred form of this esterification reaction is the reaction of a caesium salt of a compound of the formula I in which $R^2$ represents carboxy with the alcohol desired as esterifying agent in which the hydroxy group is in reactive esterified form.

Salts of compounds of the formula I can be manufactured in a manner known per se by reaction with a suitable base, for example by treatment with suitable metal compounds, such as alkali metal salts of suitable organic carboxylic acids, for example the sodium salt of -ethylcaproic acid, or with suitable inorganic alkali metal or alkaline earth metal salts, especially those derived from a weak and preferably volatile acid, for example sodium bicarbonate, or those formed with ammonia or a suitable organic amine, it being preferable to use stoichiometric amounts or only a small excess of the salt-forming agent.

Metal and ammonium salts can be converted into the free compounds in customary manner, for example by treatment with suitable acids.

Mixtures of isomers can be separated into the individual isomers in a manner known per se, for example by fractional crystallisation, chromatography, etc..

Unless stated otherwise, the processes described above, including the processes for the removal of protecting groups and the additional process steps, are carried out in a manner known per se, for example in the presence of preferably inert solvents and diluents, if necessary in the presence of condensation agents or catalysts, at reduced or elevated temperature, for example in a temperature range of from approximately $-20°$ C. to approximately $+120°$ C., especially from approximately 0° C. to approximately $+70°$ C., preferably from approximately $+10°$ C. to approximately $+40°$ C., chiefly at room temperature, in a closed vessel and/or in an inert gas atmosphere, for example a nitrogen atmosphere.

During these processes, taking into consideration all the substituents present in the molecule, if necessary, for example when readily hydrolysable radicals are present, especially gentle reaction conditions are to be applied, such as short reaction times, the use of mild acidic or basic agents in low concentration, stoichiometric quantity ratios, and the selection of suitable catalysts, solvents, temperature and/or pressure conditions.

The invention relates also to those forms of the process in which a compound obtainable as an intermediate at any stage of the process is used as starting material and the remaining process steps are carried out, or the process is interrupted at any stage, or a starting material is used in the form of a reactive derivative or salt. The starting materials used are preferably those which, in accordance with the process, result in the compounds described above as being especially valuable.

The present invention relates also to novel starting materials and/or intermediates and to processes for the manufacture thereof. The starting materials and reaction conditions are preferably so chosen that the compounds mentioned in this Application as being especially preferred are obtained.

The invention relates also to pharmaceutical preparations that contain an effective amount, especially an amount effective for the prophylaxis or therapy of virus infections or an anti-allergically or anti-inflammatorially effective amount, of the active ingredient together with pharmaceutically acceptable carriers that are suitable for topical, for example intranasal, enteral, for example oral or rectal, or parenteral administration, and may be inorganic or organic and solid or liquid. For example, tablets or gelatine capsules are used that contain the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrating agents, for example starches, agar, alginic acid or a salt thereof, such as sodium alginate, and/or effervescent mixtures, or adsorbents, colourings, flavourings and sweeteners. The pharmacologically active compounds of the present invention may also be used in the form of parenterally administrable preparations or in the form of infusion solutions. Such solutions are preferably isotonic aqueous solutions or suspensions, it being possible, for example in the case of lyophilised preparations which contain the active ingredient alone or together with a carrier, for example mannitol, to prepare these before use. The pharmaceutical preparations may be sterilised and/or contain adjuncts, for example preservatives, stabilisers, wetting agents and/or emulsifiers, solubilisers, salts for regulating the osmotic presure and/or buffers. The pharmaceutical preparations in question which, if desired, may contain other pharmacologically active substances, such as antibiotics, are manufactured in a manner known per se, for example by means of conventional mixing, granulating, confectioning, dissolving or lyophilising processes and contain approximately from 0.01% to 20%, especially from approximately 0.1% to approximately 10%, above all between 0.5% and 5%, active ingredient(s), an active ingredient concentration of less than 1% being suitable especially for preparations that are to be applied topically.

The following are preferred as forms of administration that are to be applied topically: creams, ointments or pastes, for example ointments for intranasal application or lipsticks, or preferably isotonic, sterile and physiologically tolerable solutions, for example eye drops, preferably in micro-containers to be used once, or sprays for use in the mouth or throat cavity.

The pharmaceutical preparations described in the Examples are especially suitable.

The following Examples illustrate the invention without limiting the scope thereof in any way. Unless stated otherwise, the $R_f$ values are determined on silica gel thin-layer plates (produced by Merck, Darmstadt, Germany) in the following solvent systems: A: chloroform/methanol/water (70:30:5) B: chloroform/methanol (7:3).

In the following, for example "$R_f(A)$" denotes that the $R_f$ value has been determined in system A. The spots that contain the phospholipid-containing products can be developed in a thin-layer chromatogram with modified Zinzadze reagent [specific to phospholipids; V. E. Vaskovsky and E. Y. Kostetsky, Journal of Lipid Research 9, 396 (1968)]. The ratio of the eluants to one another in the eluant mixtures used is given in parts by volume (v/v). Temperatures are given in degrees Celsius. The concentration, c, of the substance in the solvent or solvent mixture is given as a percentage (weight/volume) in the case of optical rotation. In Examples that are carried out analogously, the amounts of reactants, reagents and solvents that are not specified are in the same ratio to the corresponding amounts in the Example to which reference is made as are to each other the stated molar amounts of mutually corresponding educts in the analogy Example and in the Example to which reference is made.

Abbreviations: m.p.=melting point.

EXAMPLE 1:

To a solution of 1.40 g (2.6 mmol) of 4-(2,3,4,6-tetra-O-acetyl-β-D-glucopyranosyloxy)butyric acid in a mixture of 70 ml of chloroform and 35 ml of isopropanol there are added in succession, at 22°, 1.8 g (2.6 mmol) of 2-(1,2-dipalmitoyl-sn-glycero3-hydroxyphosphoryloxy)-ethylamine, 518 mg (3.38 mmol) of 1-hydroxybenzotriazole, 0.38 ml (2.73 mmol) of triethylamine, 700 mg (3.4 mmol) of N,N'-dicyclohexyl carbodiimide and 1.2 ml of water. The whole is stirred for 20 hours at 22° and is then concentrated by evaporation in vacuo. The oily residue is taken up in 200 ml of chloroform and the solution is washed first with 200 ml of 0.3 molar sodium phosphate buffer solution, pH 7.0, and then with saturated sodium chloride solution. After extracting the aqueous phases with a further 50 ml of chloroform, the organic phases are combined, dried over sodium sulphate, 6 ml of 3 molar methanolic sodium α-ethylhexanoate solution are added thereto and the whole is concentrated by evaporation in vacuo. From the evaporation residue taken up in 50 ml of acetone there are obtained at 0° colourless crystals which are purified by chromatography on 200 g of silica gel with chloroform/methanol/water (60:40:3). The sodium salt of 4-(2,3,4,6-tetra-O-acetyl-β-D-glucopyranosyloxy)-butyric acid 2-(1,2-dipalmitoyl-sn-glycero-3-hydroxyphosphoryloxy)-ethylamide is obtained; $R_f(B)=0.60$, $[\alpha]_D^{20}=-3.0°$ (chloroform:methanol=1:1; c=1).

The starting material is obtained in the following manner:

Stage 1.1: 49.5 g (120 mmol) of 2,3,4,6-tetra-O-acetyl-α-D-glucopyranosyl bromide and 30.2 g (143 mmol) of the silver salt of 4-hydroxyt,utyric acid [G. Wulff et al., Chemische Berichte 104, 1387–1399 (1971)] are taken up in 500 ml of absolute toluene and stirred for 40 minutes at 22° with the exclusion of light. The resulting silver bromide is filtered off and the colourless filtrate is concentrated by evaporation to an oily residue. The latter is dissolved in 750 ml of chloroform and extracted twice with 750 ml of 0.5 molar sodium bicarbonate solution each time. The aqueous phase is washed with 500 ml of chloroform and acidified from pH 8.3 to pH 3 with phosphoric acid. Extraction is carried out twice with 500 ml of chloroform each time, and the extracts are dried over sodium sulphate and concentrated by evaporation. Crystallisation from diethyl ether yields 4-(2,3,4,6-tetra-O-acetyl-β-D-glucopyranosyloxybutyric acid; m.p. 98°–100°.

EXAMPLE 2

The sodium salt of 4-(β-D-glucopyranosyloxy)-butyric acid 2-(1,2-dipalmitoyl-sn-glycero-3-hydroxyphosphoryloxy)-ethylamide is obtained analogously to Example 1 from 693 mg (2.60 mmol) of 4-(β-D-glucopyranosyloxy)-butyric acid; $R_f(A)=0.27$, $[\alpha]_D^{20}=-1.8°$ (chloroform:methanol=1:1; c=1).

The starting material is obtained in the following manner:

Stage 2.1: 1.5 g (3.4 mmol) of 4-(2,3,4,6-tetra-O-acetyl-β-D-glucopyranosyloxy)-butyric acid (see Stage 1.1) are taken up in 13 ml f chloroform and, at −10°, 22 ml of methanol containing 17.3 mmol of sodium methoxide (obtained by dissolving 400 mg of sodium) are added thereto. Stirring is carried out for 1 1/2 hours at 0° and for 1 hour at 22°. The mixture is cooled to 0°, 2 ml of water are added and the whole is adjusted to pH 3.0 with 1 molar hydrochloric acid. Concentration is carried out by evaporation in vacuo and the residue is taken up in warm ethanol and the resulting sodium chloride is filtered off. After concentrating the filtrate by evaporation, 4-(β-D-glucopyranosyloxy)butyric acid is obtained.

EXAMPLE 3

The sodium salt of 4-(2,3,4,6-tetra-O-α-D-mannopyranosyloxy)-butyric acid 2-(1,2-dipalmitoyl-sn-glycero-3-hydroxyphosphoryloxy)-ethylamide is obtained analogously to Example 1 from 1000 mg (2.30 mmol) of 4-(2,3,4,6-tetra-O-acetyl-α-D-mannopyranosyloxy)-butyric acid; $R_f(B)=0.40$, $[\alpha]_D^{20}=+3.2°$ (chloroform:methanol=1:1; c=1).

The starting material is obtained in the following manner:

Stage 3.1: 2,3,4,6-tetra-O-acetyl-D-mannosyl bromide is obtained analogously to Stage 5.1 from 10.0 g of penta-O-acetyl-D-mannose.

Stage 3.2: 4-(2,3,4,6-tetra-O-acetyl-α-D-mannopyranosyloxy)-butyric acid is obtained analogously to Stage 1.1 from 57.1 g (139 mmol) of 2,3,4,6-tetra-O-acetyl-D-mannosyl bromide; m.p. 121°–123°.

EXAMPLE 4

The sodium salt of 4-(β-D-galactopyranosyloxy)-butyric acid 2-(1,2-dipalmitoyl-sn-glycero-3-hydroxyphosphoryloxy)-ethylamide is obtained analogously to Example 1 from 580 mg (2.18 mmol) of 4-(β-D-galactopyranosyloxy)-butyric acid; $R_f(A)=0.25$, $[\alpha]_D^{20}=+2.2°$ (chloroform:methanol=1:1; c=1).

The starting material is obtained in the following manner:

Stage 4.1: 4-(2,3,4,6-tetra-O-acetyl-β-D-galactopyranosyloxy)-butyric acid is obtained analogously to Stage 1.1 from 49.3 g (120 mmol) of 2,3,4,6-tetra-O-acetyl-α-D-galactopyranosyl bromide; m.p. 57°–60°.

Stage 4.2: 4-(β-D-galactopyranosyloxy)-butyric acid is obtained analogously to Stage 2.1 from 4-(2,3,4,6-tetra-O-acetyl-β-D-galactopyranosyloxy)-butyric acid.

EXAMPLE 5

The sodium salt of 4-(β-D-cellobiopyranosyloxy)-butyric acid 2-(1,2-dipalmitoyl-sn-glycero-3-hydroxyphosphoryloxy)-ethylamide is obtained analogously to Example 1 from 700 mg (1.63 mmol) of 4-(β-D-cellobiopyranosyloxy)-butyric acid; $R_f(A)=0.20$, $[\alpha]_D^{20}=-1.1°$, (chloroform:methanol=1:1; c=1).

The starting material is obtained in the following manner:

Stage 5.1: Analogously to the instructions of E. Fischer, Ber. Dtsch. Chem. Ges. 49, 584–585 (1916), 27.8 g (41 mmol) of octa-O-acetyl-D-cellobiose are taken up in 60 ml of glacial acetic acid, and 40 ml of methylene chloride and 41 ml of a 33% solution of hydrogen bromide in glacial acetic acid are added thereto. After stirring for 15 minutes at 22°, the suspension goes into solution. After stirring for a total of 2½ hours at 22°, the solution is poured onto 500 ml of ice-water. The mixture is extracted three times with 500 ml of chloroform each time. The organic phases are repeatedly washed neutral with ice-water, then dried over magnesium sulphate and concentrated by evaporation. Crystallisation from diethyl ether yields hepta-O-acetyl-α-D-cellobiopyranosyl bromide; m.p. 190°–191°.

Stage 5.2: 4-(hepta-O-acetyl-β-D-cellobiopyranosyloxy)butyric acid is obtained analogously to Stage 1.1 from 16.0 g (22.9 mmol) of hepta-O-acetyl-α-D-cellobiopyranosyl bromide.

Stage 5.3: 4-(β-D-cellobiopyranosyloxy)-butyric acid is obtained analogously to Stage 2.1 from 4-(hepta-O-acetyl-β-D-cellobiopyranosyloxy)-butyric acid.

EXAMPLE 6

The sodium salt of 4-(β-D-lactopyranosyloxy)-butyric acid 2-(1,2-dipalmitoyl-sn-glycero-3-hydroxyphoshoryloxy)-ethylamide is obtained analogously to Example 1 from 700 mg (1.63 mmol) of 4-(β-D-lactopyranosyloxy)-butyric acid; $R_f(A)=0.23$, $[\alpha]_D^{20}=+2.1°$, (chloroform:methanol=1:1; c=1)

The starting material is obtained in the following manner:

Stage 6.1: Hepta-O-acetyl-α-D-lactopyranosyl bromide is obtained analogously to Stage 5.1 from 6.9 g of octa-O-acetyl-β-D-lactopyranose; m.p. 139°–140°.

Stage 6.2: 4-(hepta-O-acetyl-β-D-lactopyranosyloxy)butyric acid is obtained analogously to Stage 1.1 from 16.0 g (22.9 mmol) of hepta-O-acetyl-α-D-lactopyranosyl bromide.

Stage 6.3: 1.5 g of crude 4-(hepta-O-acetyl-β-D-lactopyranosyloxy)-butyric acid are dissolved in 15 ml of chloroform and, after adding 0.83 ml of a 3 molar methanolic sodium α-ethylhexanoate solution, stirring is carried out for 10 minutes. The whole is then concentrated by evaporation, repeatedly digested with diethyl ether and the crystalline sodium salt of 4-(hepta-O-acetyl-β-D-lactopyranosyloxy)-utyric acid is obtained.

Stage 6.4: 4-(β-D-lactopyranosyloxy)-butyric acid is obtained analogously to Stage 2.1 from the sodium salt of 4-(hepta-O-acetyl-β-D-lactopyranosyloxy)-butyric acid.

EXAMPLE 7

The sodium salt of 4-(β-D-maltopyranosyloxy)-butyric acid 2-(1,2-dipalmitoyl-sn-glycero-3-hydroxyphosphoryloxy)-ethylamide is obtained analogously to Example 1 from 700 mg (1.63 mmol) of 4-(β-D-maltopyranosyloxy)-butyric acid; $R_f(A)=0.33$, $[\alpha]_D^{20}=+28.4°$ (chloroform:methanol=1:1; c=1).

The starting material is obtained in the following manner:

Stage 7.1: Hepta-O-acetyl-α-D-maltopyranosyl bromide is obtained analogously to Stage 5.1 from 37.0 g of octa-O-acetyl-D-maltopyranose.

Stage 7.2: 4-(hepta-O-acetyl-β-D-maltopyranosyloxy)butyric acid is obtained analogously to Stage 1.1 from hepta-O-acetyl-α-D-maltopyranosyl bromide.

Stage 7.3: The sodium salt of 4-(hepta-O-acetyl-β-D-maltopyranosyloxy)-butyric acid is obtained analogously to Stage 6.3 from 4-(hepta-O-acetyl-β-D-maltopyranosyloxy)-butyric acid.

Stage 7.4: 4-(β-D-maltopyranosyloxy)-butyric acid is obtained analogously to Stage 2.1 from the sodium salt of 4-(hepta-O-acetyl-β-D-maltopyranosyloxy)-butyric acid.

EXAMPLE 8

The sodium salt of 4-(β-L-fucopyranosyloxy)-butyric acid 2-(1,2-dipalmitoyl-sn-glycero-3-hydroxyphosphoryloxy)-ethylamide is obtained analogously to Example 1 from 600 mg (2.40 mmol) of 4-(B-L-fucopyranosyloxy)-butyric acid; $R_f(A)=0.37$, $[\alpha]_D^{20}=+9.4°$ (chloroform:methanol=1:1; c=1).

The starting material is obtained in the following manner:

Stage 8.1: Tri-O-acetyl-L-fucosyl bromide is obtained analogously to Stage 5.1 from 27.6 g of tetra-O-acetyl-L-fucose.

Stage 8.2: 4-(2,3,4-tri-O-acetyl-β-L-fucopyranosyloxy)butyric acid is obtained analogously to Stage 1.1 from 26.5 g (75.0 mmol) of tri-O-acetyl-L-fucosyl bromide.

Stage 8.3: The sodium salt of 4-(2,3,4-tri-O-acetyl-β-L-fucopyranosyloxy)-butyric acid is obtained analogously to Stage 6.3 from 4-(2,3,4-tri-O-acetyl-β-L-fucopyranosyloxy)-butyric acid.

Stage 8.4: 4-(β-L-fucopyranosyloxy)-butyric acid is obtained analogously to Stage 2.1 from 4-(2,3,4-tri-O-acetyl-β-L-fucopyranosyloxy)-butyric acid.

EXAMPLE 9

The sodium salt of 4-(2-acetylamino-2-deoxy-β-D-glucopyranosyloxy)-butyric acid 2-(1,2-dipalmitoyl-sn-glycero-3-hydroxyphosphoryloxy)-ethylamide is obtained analogously to Example 1 from 4-(2-acetylamino-2-deoxy-β-D-glucopyranosyloxy)-butyric acid.

The starting material is obtained in the following manner:

Stage 9.1: 4-(2-acetylamino-3,4,6-tri-O-acetyl-2-deoxy)-β-D-glucopyranosyloxy)-butyric acid is obtained analogously to Stage 1.1 from 2-acetylamino-3,4,6-triacetyl-2-deoxy-α-D-glucopyranosyl bromide [prepared according to J. W. Gillard et al., Tetrahedron Lett. 22, 513 (1981)].

Stage 9.2: 4-(2-acetylamino-2-deoxy-β-D-glucopyranosyloxy)-butyric acid is obtained analogously to Stage 2.1 from 4-(2-acetylamino-3,4,6-tri-O-acetyl-2-deoxy)-β-D-glucopyranosyloxy)-butyric acid.

EXAMPLE 10

The sodium salt of N-[4-(β-D-galactopyranosyloxy)-butyryl]-glycine 2-(1,2-dipalmitoyl-sn-glycero-3-hydroxyphosphoryloxy)-ethylamide is obtained analogously to Example 1 from 518 mg (1.60 mmol) of N-[4-(β-D-galactopyranosyloxy)butyryl]-glycine; $R_f(A)=0.27$, $[\alpha]_D^{20}=+1.4°$ (chloroform:methanol=1:1; c=1).

The starting material is obtained in the following manner:

Stage 10.1: 516 mg (3.37 mmol) of 1-hydroxybenzotriazole and 695 mg (3.37 mmol) of N,N'-dicyclohexyl carbodiimide are added to a solution of 640 mg (2.59 mmol) of 4-(β-D-galactopyranosyloxy)-butyric acid in 4 ml of N,N-dimethylformamide and 4 ml of chloroform and the whole is stirred for 2 hours at 22°. There is then added a solution prepared at pH 10.6 by adding normal sodium hydroxide solution to 194 mg (2.59 mmol) of glycine and 2 ml of water, and the whole is then stirred for 18 hours at 22°. The mixture is concentrated by evaporation under a high vacuum, and the residue is taken up in a small amount of N,N-dimethylformamide and, after stirring briefly at 0°, is freed of insoluble material by filtration. Having concentrated the filtrate by evaporation, digestion with acetone yields 618 mg of the sodium salt of N-[4-(β-D-galactopyranosyloxy)-butyryl]-glycine in the form of a white powder.

Stage 10.2: A solution of 600 mg of the sodium salt of N-[4-(β-D-galactopyranosyloxy)-butyryl]-glycine in 10 ml of methanol/water (1:1) is adjusted, at 0°, to pH 2.5 with 1 normal hydrochloric acid and concentrated by evaporation in vacuo. The residue, dissolved in warm ethanol, is filtered until clear and in the filtrate, which is concentrated by evaporation, N-[4-(β-D-galactopyranosyloxy)-butyryl]-glycine is obtained.

EXAMPLE 11

Analogously to Example 1, but using chloroform/methanol/water (70:30:5) as eluant in the chromatography, the sodium salt of 4-(β-D-cellobiopyranosyloxy)-butyric acid 2-(1,3-di-n-dodecanoylglycero-2-hydroxyphosphoryloxy)-ethylamide is obtained from 591 mg (1.38 mmol) of 4-(β-D-cellobiopyranosyloxy)-butyric acid (see Stage 5.3) and 800 mg (1.38 mmol) of 2-(1,3-di-n-dodecanoyl-glycero-2-hydroxyphosphoryloxy)-ethylamine; $R_f(A)=0.25$, $[\alpha]_D^{20}=-6.9°$ (chloroform:methanol=1:1; c=1).

EXAMPLE 12

A solution of 1000 mg (3.26 mmol) of 4-(α-D-mannopyranosylthio)-butyric acid, 0.74 g (4.9 mmol) of 1-hydroxybenzotriazole (containing 12% water) and 1.4 g (6.6 mmol) of N,N'-dicyclohexyl carbodiimide in 50 ml of N,N-dimethylformamide is stirred for 3 hours at 22°. The mixture is concentrated by evaporation under a high vacuum and the oily residue is digested three times with 50 ml of diethyl ether each time. The resulting colourless, crystalline residue is taken up in 30 ml of isopropanol and, at 22°, there is added dropwise thereto, within a period of 10 minutes, a solution of 1.86 g (2.61 mmol) of the sodium salt of 2-(1,2-dipalmitoyl-sn-glycero-3-hydroxyphosphoryloxy)ethylamine in 50 ml of chloroform/isopropanol (9:1). Stirring is then carried out for 30 minutes, 8 ml of water are added and stirring is carried out for a further 2 hours at 22°. Analogously to Example 1, 6 ml of 3 molar sodium α-ethylhexanoate solution are added to the mixture, the whole is then concentrated by evaporation, crystallised from acetone and then chromatographed as described therein. The sodium salt of 4-(α-D-mannopyranosylthio)-butyric acid 2-(1,2-dipalmitoyl-sn-glycero-3-hydroxyphosphoryloxy)-ethylamide is obtained; $R_f(A)=0.41$; $[\alpha]_D^{20}=+67°$; (methanol; c=0.66).

The starting material is obtained as follows:

Stage 12.1: A mixture of 90 g (0.185 mol) of S-(2,3,4,6-tetra-O-acetyl-α-D-mannopyranosyl)-isothiuronium bromide [K. L. Matta et al., Carbohydrate Research 43, 101 (1975); P. L. Durette et al., Carbohydrate Research 81, 261 (1980)], 42.6 g (0.199 mol) of 4-iodobutyric acid, 29.6 g (0.215 mol) of potassium carbonate and 37 g (0.187 mol) of potassium disulphite ($2K_2S_2O_5 \cdot 3H_2O$) in 150 ml of acetone and 150 ml of water is stirred for 1 hour at 22°. 700 ml of 5% hydrochloric acid and 700 ml of chloroform are added and the whole is stirred for 5 minutes. The organic phase is separated off, dried over sodium sulphate and concentrated by evaporation. The oily residue contains 4-(2,3,4,6-tetra-O-acetyl-α-D-mannopyranosylthio)-butyric acid.

Stage 12.2: 4-(e-D-mannopyranosylthio)-butyric acid is obtained analogously to Stage 2.1 from 4-(2,3,4,6-tetra-O-acetyl-α-D-mannopyranosylthio)-butyric acid.

EXAMPLE 13

The sodium salt of 4-(α-D-mannopyranosyloxy)-butyric acid 2-(1,2-dipalmitoyl sn-glycero-3-hydroxyphosphoryloxy)-ethylamide is obtained analogously to Example 12 from 4-(α-D-mannopyranosyloxy)-butyric acid (see Stage 3.2).

EXAMPLE 14

Analogously to Example 2, there are obtained from 4-(β-D-glucopyranosyloxy)-butyric acid and corresponding phosphatidyl compounds the disodium salt of 4-(β-D-glucopyranosyloxy)-butyryl]-O-(1,2-dioleoyl-sn-glycero-3-hydroxyphosphoryl)-L-serine, the disodium salt of N-[4-(β-D-glucopyranosyloxy)-butyryl]-O-(1,3-di-n-dodecanoyl-glycero-2-hydroxyphosphoryl)-L-serine, the sodium salt of 4-(β-D-glucopyranosyloxy)butyric acid 2-(2-n-decanoyloxy-ethoxy-hydroxyphosphoryloxy)-ethylamide, the sodium salt of 4-(β-D-glucopyranosyloxy)-butyric acid 2-(1,2-di-stearoyl-sn-glycero-3-hydroxyphosphoryloxy)-ethylamide, the sodium salt of 4-(β-D-glucopyranosyloxy)-butyric acid 2-(1,2-diarachinoyl-sn-glycero-3-hydroxyphosphoryloxy)-ethylamide, the sodium salt of 4-(β-D-glucopyranosyloxy)-butyric acid 2-(1,2-dimyristoyl-sn-glycero-3-hydroxyphosphoryloxy)-ethylamide, the sodium salt of 4-(β-D-glucopyranosyloxy)-butyric acid 2-(1,2-dilauroyl-sn-glycero-3-hydroxyphosphoryloxy)-ethylamide, the sodium salt of 4-(β-D-glucopyranosyloxy)-butyric acid 2-(1-palmitoyl-2-oleoyl-sn-glycero-3-hydroxyphosphoryloxy)-ethylamide and the sodium salt of 4-(β-D-glucopyranosyloxy)-butyric acid 2-(1-palmitoyl-glycero-3-hydroxyphosphoryloxy)ethylamide.

EXAMPLE 15

Nasal ointment

| Composition | |
|---|---|
| the sodium salt of 4-(β-D-maltopyranosyloxy)-butyric acid 2-(1,2-dipalmitoyl-sn-glycero-3-hydroxyphosphoryloxy)-ethylamide | 0.50 g |
| paraffin oil, viscous | 20.00 g |
| white petroleum jelly | 30.00 g |
| wool fat, anhydrous | 40.00 g |
| demineralised water | 19.50 g |

Manufacture

The fatty phase, consisting of the paraffin oil, petroleum jelly and wool fat, is melted together. The aqueous solution of the active ingredient is incorporated into the fatty phase at approximately 50° C.

EXAMPLE 16

The sodium salt of 2-(2-acetylamino-2-deoxy-β-D-glucopyranosyloxy)-acetic acid 2-(1,2-dipalmitoyl-sn-glycero-3-hydroxyphosphoryloxy)-ethylamide is obtained analogously to Example 1 from 1.344 g (4.57 mmol) of 2-(2-acetylamino-2-deoxy-β-D-glucopyranosyloxy)-acetic acid; $R_f(A)=0.37$; $[\alpha]_D^{20}=-15.2°$ (chloroform:methanol=1:1; c=1).

The starting material is obtained in the following manner:

Stage 16.1: A solution of 600 mg (1.82 mmol) of 2-methyl-(3,4,6-tri-O-acetyl-1,2-dideoxy-α-D-glucopyrano)-[2,1-d]-2-oxazoline of the formula

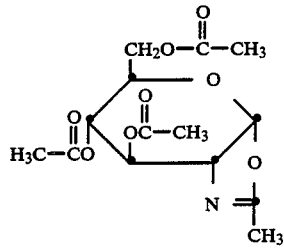

[prepared according to V. K. Srivastava, Carbohydrate Research 103, 286 (1982)]and 605 mg (3.64 mmol) of glycolic acid benzyl ester in 6 ml of methylene chloride is added to a solution of 300 mg (1.85 mmol) of iron(III) chloride (anhydrous) in 6 ml of absolute methylene chloride and the whole is stirred for 21 hours at 22°. 8 ml of cold, saturated sodium bicarbonate solution are added and the mixture is diluted with 100 ml of chloroform and filtered until clear. The organic phase of the filtrate yields, after drying over magnesium sulphate and concentration by evaporation, a yellow oil which is purified by digesting an ethyl acetate solution with hexane and by chromatography on silica gel. 2-(2-acetylamino-3,4,6-tri-O-acetyl-2-deoxy-β-D-glucopyranosyloxy)-acetic acid benzyl ester is obtained in the form of a colourless powder.

Stage 16.2: A sodium methoxide solution, prepared by dissolving 472 mg (27.5 mmol) of sodium in 20 ml of absolute methanol, is added at 0° to a solution of 2.54 g (6.87 mmol) of 2-(2-acetylamino-3,4,6-tri-O-acetyl-2-deoxy-β-D-glucopyranosyloxy)-acetic acid benzyl ester in 60 ml of absolute methanol and stirring is carried out for 2 1/2 hours at 0° and for 1 hour at 22°. The mixture is concentrated by evaporation in vacuo, and the residue is dissolved in a small amount of methanol and precipitated with diethyl ether. The resulting crude sodium salt is dissolved in 60 ml of methanol/water (2:1) and, at 0°, acidified to pH 3.1 with 1 normal hydrochloric acid. The mixture is concentrated by evaporation, taken up in ethanol/chloroform (1:1), filtered until clear, concentrated by evaporation again, taken up in ethanol, clarified and precipitated with ethyl acetate/hexane. 2-(2-acetyl- amino-2-deoxy-β-D-glucopyranosyloxy)-acetic acid is obtained in the form of a whitish powder.

EXAMPLE 17

Female balb/c mice (in the case of active substance A) and MF-2f SPF mice (in the case of active substance B) weighing 14–16 g are infected intranasally, under light anaesthetic with a mixture of equal parts of diethyl ether, ethanol and chloroform, with lethal doses (approximately LD$_{95}$) in the form of 0.05 ml each of a suspension of influenza A/Texas/1/77 viruses (mouse-adapted strain).

The amount stated in Table 1 of the particular active substance in 0.05 ml, in the case of intranasal administration, and in 0.2 ml, in the case of oral administration, of a 0.005% by weight solution of the sodium salt of carboxymethylcellulose in double-distilled, pyrogen-free water is administered once (single dose), in the manner stated in Table 1, to each mouse from groups each comprising 10 of these mice at the specified time [days] related to the day of infection.

20 of the above-mentioned infected mice in each case are used as the control, that is to say they receive a placebo (0.005 % by weight solution of the sodium salt of carboxymethylcellulose).

The intranasal administration of the active substance is carried out under light anaesthetic with a mixture of equal parts of diethyl ether, ethanol and chloroform.

Active substance A=the sodium salt of 4-(β-D-maltopyranosyloxy)-butyric acid 2-(1,2-dipalmitoyl-sn-glycero-3-hydroxyphosphoryloxy)-ethylamide.

Active substance B=the sodium salt of 4-(β-D-mannopyranosylthio)-butyric acid 2-(1,2-dipalmitoyl-sn-glycero-3-hydroxyphosphoryloxy)-ethylamide.

The results can be seen in the following Table.

| active substance | method of administration | time of administration [days] | percentage of the mice still surviving 23 days (active substance B) and 24 days (active substance A) after infection as a function of the amount of active substance [mg/kg], statistical significance * P ≦ 0.05, ** P ≦ 0.01 (Vierfelder Test), n.t. = not tested | | | |
|---|---|---|---|---|---|---|
| | | | 0.1 | 0.01 | 0.001 | 0 = control |
| A | oral | +7 | 80** | 70** | 50* | 5 |
| B | intra-nasal | −7 | 80** | 90** | 50* | 5 |

We claim:
1. A saccharide derivative of the formula I

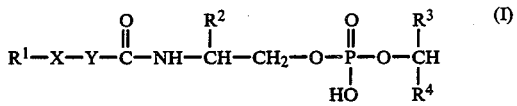

in which R¹ represents a) aldohexosyl, (b) D-aldohexosyl that is glycosidically linked in the 4- or the 6-position to D-aldohexosyl, (c) aldopentosyl, (d) 6-deoxy-aldohexosyl or (e) 2-acetylamino-2-deoxy-D-aldohexosyl, it being possible for free hydroxy groups present in the radicals mentioned under a) to e) above to be peracetylated, X represents oxygen or sulphur, Y represents alkylene having up to 10 carbon atoms in which from 1 to 3 non-terminal methylene groups may be replaced by oxygen, by carbonylimino or by carbonyloxy, R² represents hydrogen, carboxy, lower alkoxycarbonyl, benzyloxycarbonyl or carbamoyl, R³ represents hydrogen and R⁴ represents a 1,2-dihydroxyethyl, 2-hydroxy-ethyl or hydroxymethyl group in which at least one hydroxy group is esterified by an unsubstituted aliphatic $C_{10-24}$-carboxylic acid and in which the other hydroxy group, if present, is free or esterified by an aliphatic $C_{2-24}$-carboxylic acid, or R³ and R⁴ each represents a hydroxymethyl group esterified by an unsubstituted aliphatic $C_{10-24}$-carboxylic acid, or a pharmaceutically acceptable salt thereof, or a mixture of said saccharide derivative and its pharmaceutically acceptable salt.

2. A compound of the formula I according to claim 1, in which R³ represents hydrogen and R⁴ represents 1,2-dihydroxy-ethyl in which either only the 2-hydroxy group or both hydroxy groups independently of each other are esterified by a $C_{10-24}$-alkanoic acid or by a $C_{18}$-alkenoic acid, or R³ and R⁴ each represents hydroxymethyl esterified by a $C_{10-24}$-alkanoic acid or a $C_{18}$-alkenoic acid, and the other substituents have the meanings mentioned in claim 1, or a pharmaceutically acceptable salt thereof, or a mixture of said compound of the formula I and its pharmaceutically acceptable salt.

3. A compound of the formula I according to claim 1, in which R³ represents hydrogen and R⁴ represents 1,2-dihydroxyethyl in which both hydroxy groups independently of each other are esterified by a $C_{10-24}$-alkanoic acid or a $C_{18}$-alkenoic acid, or R³ and R⁴ each represents hydroxymethyl esterified by a $C_{10-24}$-alkanoic acid or by a $C_{18}$-alkenoic acid, and the other substituents have the meanings mentioned in claim 1, or a pharmaceutically acceptable salt thereof, or mixture of said compound of the formula I and its pharmaceutically acceptable salt.

4. A compound of the formula I according to claim 1, in which R³ represents hydrogen and R⁴ represents 1,2-dihydroxyethyl in which both hydroxy groups independently of each other are esterified by an unbranched $C_{10-24}$-alkanoic acid having an even number of carbon atoms or by an unbranched $C_{18}$-alkenoic acid having from 1 to 3 isolated double bonds, or R³ and R⁴ each represents hydroxymethyl esterified by an unbranched $C_{10-24}$-alkanoic acid having an even number of carbon atoms or by an unbranched $C_{18}$-alkenoic acid having from 1 to 3 isolated double bonds, and the other substituents have the meanings mentioned in claim 1, or a pharmaceutically acceptable salt thereof, or a mixture of said compound of the formula I and its pharmaceutically acceptable salt.

5. A compound of the formula I according to claim 1, in which Y represents unbranched $C_1$-$C_5$-alkylene or the radical —$CH_2$—$CH_2$—$CH_2$—CO—NH—$CH_2$—, or a pharmaceutically acceptable salt thereof, or a mixture of said compound of the formula I and its pharmaceutically acceptable salt.

6. A compound of the formula I according to claim 1, in which R¹ represents a) D-aldohexosyl that may be glycosidically linked in the 4-position to D-aldohexosyl, (b) 6-deoxy-aldohexosyl or (c) 2-acetylamino-2-deoxy-D-aldohexosyl, it being possible for free hydroxy groups present in the radicals mentioned under (a) to (c) above to be peracetylated, X represents oxygen or sulphur, Y represents $C_{3-5}$-alkylene in which a non-terminal methylene group may be replaced by carbonylimino, R² represents hydrogen or carboxy, R³ represents hydrogen and R⁴ represents 1,2-dihydroxyethyl in which either only the 2-hydroxy group or both hydroxy groups independently of each other are esterified by an unbranched $C_{10-24}$-alkanoic acid or by an unbranched $C_{18}$-alkenoic acid, or R³ and R⁴ each represents hydroxymethyl esterified by an unbranched $C_{10-24}$alkanoic acid or by an unbranched $C_{18}$-alkenoic acid having from 1 to 3 isolated double bonds, or a pharmaceutically acceptable salt thereof, or a mixture of said compound of the formula I and its pharmaceutically acceptable salt.

7. A compound of the formula I according to claim 1, in which R1 represents (a) D-aldohexosyl in which free hydroxy groups may be peracetylated, (b) D-aldohexosyl that is glycosidically linked in the 4-position to D- aldohexosyl, (c) 6-deoxy-aldohexosyl or (d) 2-acetylamino-2-deoxy-D-aldohexosyl, X represents oxygen or sulphur, Y represents alkylene having up to 5 carbon atoms in which a non-terminal methylene group may be replaced by carbonylimino, $R^2$ represents hydrogen or carboxy, $R^3$ represents hydrogen and $R^4$ represents 1,2-dihydroxyethyl in which both hydroxy groups are esterified by an unbranched $C_{10}$–$C_{20}$-alkanoic acid having an even number of carbon atoms or by oleic acid, or $R^3$ and $R^4$ each represents hydroxymethyl esterified by an unbranched $C_{10}$–$C_{20}$-alkanoic acid having an even number of carbon atoms or by oleic acid, or a pharmaceutically acceptable salt thereof, or a mixture of said compound of the formula I and its pharmaceutically acceptable salt.

8. A pharmaceutically acceptable salt according to claim 1 of a compound of the formula I, in which $R^1$ represents D-glucosyl, 2,3,4,6-tetra-O-acetyl-D-glucosyl, D-mannosyl, 2,3,4,6-tetra-O-acetyl-D-mannosyl, D-galactosyl, D-cellobiosyl, D-lactosyl, D-maltosyl, L-fucosyl or 2-acetylamino-2-deoxy-D-glucosyl, or a mixture of said salt and said compound of the formula I.

9. A pharmaceutically acceptable salt according to claim 1 of a compound of the formula I, in which $R^1$ represents 2,3,4,6-tetra-O-acetyl-$\beta$-D-glucopyranosyl, $\beta$-D-glucopyranosyl, 2,3,4,6-tetra-O-acetyl-$\alpha$-D-mannopyranosyl, $\beta$-D-galactopyranosyl, $\beta$-D-cellobiopyranosyl, $\beta$-D-lactopyranosyl, $\beta$-D-maltopyranosyl, $\beta$-L-fucopyranosyl, 2-acetylamino-2-deoxy-$\beta$-D-glucopyranosyl or $\alpha$-D-mannopyranosyl, X represents oxygen or sulphur, Y represents trimethylene, methylene or —CH$_2$—CH$_2$—CH$_2$—CONH—CH$_2$—, $R^2$ represents hydrogen or carboxy, $R^3$ represents hydrogen and $R^4$ represents 1,2-di-lauroyloxy-ethyl, 1,2-dimyristoyloxy-ethyl, 1,2-di-palmitoyloxy-ethyl, 1,2-distearoyloxy-ethyl, 1,2-n-eicosanoyloxy-ethyl, 1,2-dioleoyloxy-ethyl, n-decanoyloxy-methyl or 2-palmitoyloxy-ethyl, or $R^3$ and $R^4$ each represents lauroyloxymethyl, or a mixture of said salt and said compound of the formula I.

10. A pharmaceutically acceptable salt according to claim 9 of a compound of the formula I, in which $R^2$ represents hydrogen.

11. A pharmaceutically acceptable salt according to claim 10 of a compound of the formula I, in which Y represents trimethylene or the radical —CH$_2$—CH$_2$—CO—NH—CH$_2$—.

12. A pharmaceutically acceptable salt according to claim 1 of a compound of the formula I, in which $R^3$ represents hydrogen and $R^4$ represents 1,2-dipalmitoyloxy-ethyl or $R^3$ and $R^4$ each represents lauroyloxymethyl.

13. The sodium salt of 4-(2,3,4,6-tetra-O-acetyl-$\beta$-D-glucopyranosyloxy)-butyric acid 2-(1,2-dipalmitoyl-sn-glycero-3-hydroxyphosphoryloxy)-ethylamide according to claim 1.

14. The sodium salt of 4-($\beta$-D-glucopyranosyloxy)-butyric acid 2-(1,2-dipalmitoyl-sn-glycero-3-hydroxyphosphoryloxy)-ethylamide according to claim 1.

15. The sodium salt of 4-(2,3,4,6-tetra-O-acetyl-$\alpha$-D-mannopyranosyloxy)-butyric acid 2-(1,2-dipalmitoyl-sn-glycero-3-hydroxyphosphoryloxy)-ethylamide according to claim 1.

16. The sodium salt of 4-($\beta$-D-galactopyranosyloxy)-butyric acid 2-(1,2-dipalmitoyl-sn-glycero-3-hydroxyphosphoryloxy)-ethylamide according to claim 1.

17. The sodium salt of 4-(3-D-cellobiopyranosyloxy)-butyric acid 2-(1,2-dipalmitoyl-sn-glycero-3-hydroxyphosphoryloxy)-ethylamide according to claim 1.

18. The sodium salt of 4-($\beta$-D-lactopyranosyloxy)-butyric acid 2-(1,2-dipalmitoyl-sn-glycero-3-hydroxyphosphoryloxy)-ethylamide according to claim 1.

19. The sodium salt of 4-($\beta$-D-maltopyranosyloxy)-butyric acid 2-(1,2-dipalmitoyl-sn-glycero-3-hydroxyphosphoryloxy)-ethylamide according to claim 1.

20. The sodium salt of 4-($\beta$-L-fucopyranosyloxy)-butyric acid 2-(1,2-dipalmitoyl-sn-glycero-3-hydroxyphosphoryloxy)-ethylamide according to claim 1.

21. The sodium salt of N-[4-($\beta$-D-galactopyranosyloxy)butyryl]-glycine 2-(1,2-dipalmitoyl-sn-glycero-3-hydroxyphosphoryloxy)-ethylamide according to claim 1.

22. The sodium salt of 4-($\beta$-D-cellobiopyranosyloxy)-butyric acid 2-(1,3-di-n-dodecanoyl-glycero-2-hydroxyphosphoryloxy)-ethylamide according to claim 1.

23. The sodium salt of 4-(c-D-mannopyranosylthio)-butyric acid 2-(1,2-dipalmitoyl-sn-glycero-3-hydroxyphosphoryloxy)-ethylamide according to claim 1.

24. The sodium salt of 2-(2-acetylamino-2-deoxy-$\beta$-D-glucopyranosyloxy)-acetic acid 2-(1,2-dipalmitoyl-sn-glycero-3-hydroxyphosphoryloxy)-ethylamide according to claim 1.

25. A pharmaceutical preparation for the prophylaxis or therapy of a virus infection in or on a warm-blooded animal containing an in vivo antivirally effective amount of a pharmaceutically acceptable salt according to claim 1 together with a pharmaceutical carrier.

26. Method for the prophylaxis or therapy of and infection caused by influenza A viruses in or on a warm-blooded animal comprising administering to said animal an in vivo antivirally effective amount of a pharmaceutically acceptable salt of 4($\beta$-Dmalto-pyranosyloxy)-butyric acid 2-(1,2-dipalmitoyl-sn-glycero-3-hydroxphosphoryloxy)-ethylamide.

27. Method for the prophylaxis or therapy of and infection caused by influenza A viruses in or on a warm-blooded animal comprising administering to said animal an in vivo antivirally effective amount of a pharmaceutically acceptable salt of 4-($\alpha$-D-manno-pyranosylthio)-butyric acid 2-(1,2-dipalmitoyl-sn-glycero-3-hydroxyphosphoryloxy)-ethylamide.

* * * * *